United States Patent [19]
Zhu

[11] Patent Number: 5,695,465
[45] Date of Patent: Dec. 9, 1997

[54] SYRINGE CONTAINING DRUG TO BE INJECTED

[76] Inventor: Jinyou Zhu, 1-301, Kunminglu Road, Heping District, Tianjin 300051, China

[21] Appl. No.: 565,283

[22] Filed: Nov. 30, 1995

[30] Foreign Application Priority Data

Jul. 24, 1995 [CN] China ................... 95216467.1

[51] Int. Cl.$^6$ ................................................ A61M 31/00
[52] U.S. Cl. ........................ 604/82; 604/85; 604/89; 604/202; 604/236; 604/246
[58] Field of Search ......................... 604/83, 85, 87, 604/89–91, 131, 140–1, 143, 146–9, 181–4, 187, 197, 200–6, 218, 222, 226–9, 231, 233–4, 236–7, 249, 256; 137/845

[56] References Cited

U.S. PATENT DOCUMENTS

| | | | |
|---|---|---|---|
| 3,548,824 | 12/1970 | Carr. | |
| 4,331,146 | 5/1982 | Brignola | 604/200 |
| 4,934,379 | 6/1990 | Marzolf et al. | 604/231 |
| 5,015,229 | 5/1991 | Meyer et al. | 604/231 |
| 5,181,909 | 1/1993 | McFarlane | 604/52 |

FOREIGN PATENT DOCUMENTS

| | | |
|---|---|---|
| 90 2 05143.1 | 11/1990 | China. |
| 92 2 03096.0 | 9/1992 | China. |
| 93 1 05563.6 | 11/1994 | China. |
| 93 1 09125.X | 2/1995 | China. |

*Primary Examiner*—Michael Powell Buiz
*Assistant Examiner*—Bhisma Mehta
*Attorney, Agent, or Firm*—Tilton, Fallon, Lungmus & Chestnut

[57] ABSTRACT

A syringe containing drug to be injected, the syringe includes an injection tube, a needle mounted at the front end of the injection tube, a rubber sealing jacket stopper jacketing on the peak of the needle and an injection tube core movably and hermetically put inside the injection tube, which is characterized in that the injection tube core consists of an ampule of cylindrical bottle shape and a piston, the back end of the ampule is closed and at its front end there are a flange and a neck portion, the central through hole of the flange and the neck portion is interpenetrated with the inner cavity of the bottle-shaped injection tube core; the outside top of the piston appears as a cone, and its outside lower part is a cylinder matching the inner wall of the injection tube, while the inside top of the piston appears as an inner cone, and the form of its inside lower part matches the shapes of the flange and the neck portion located at the front end of the ampule; at the cone-shaped top of the piston there is a slit linking up the inside and the outside of the top and inclined to the axis of the piston, so that a one-way valve which could be opened outwardly is formed at the cone-shaped top.

3 Claims, 2 Drawing Sheets

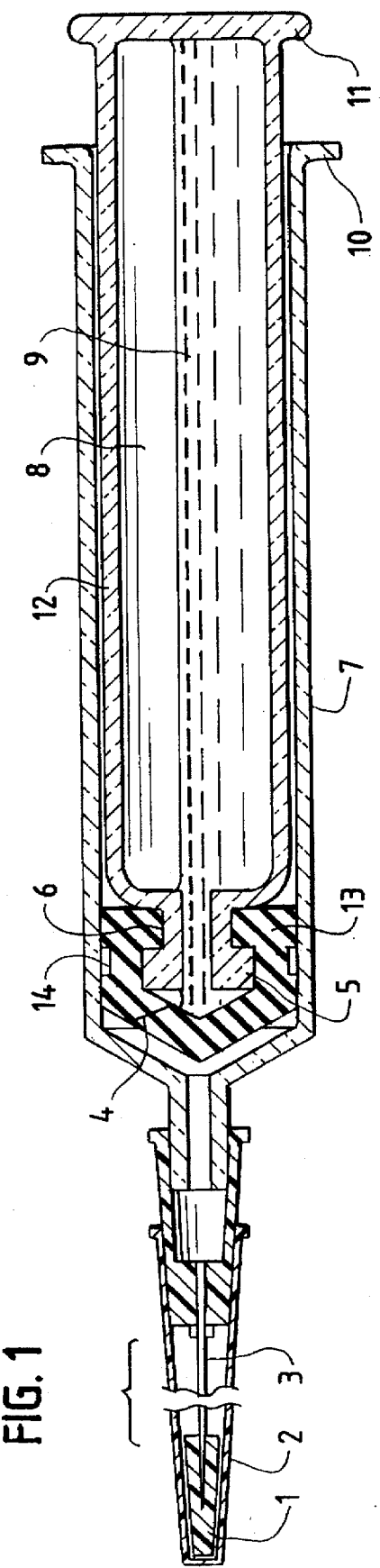
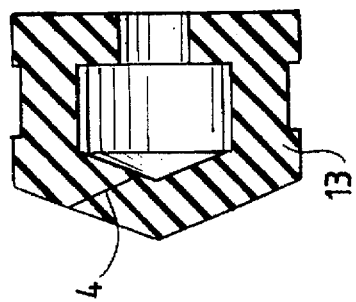
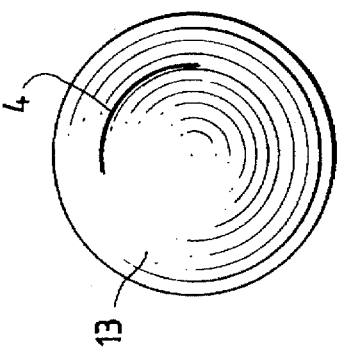
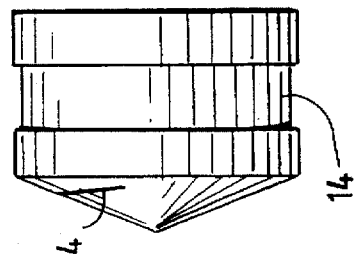

SYRINGE CONTAINING DRUG TO BE INJECTED

BACKGROUND OF THE INVENTION

1. Field of the Invention

This invention relates to a medical syringe, especially to a disposable syringe containing drug to be injected, particularly to a syringe, which has been provided with two functions for injecting and containing drug, i.e. which is both a bottle for storing and transporting drug, namely so-called ampule, and a drug syringe for injecting drug into the body in need of injection.

2. Prior Art

The medical and disposable aseptic syringe in present clinical usage includes an injection tube and an injection tube core, one end of the injection tube is open and at its other end there is a nipple for mounting needle, the injection tube core is movable and hermetically put in the injection tube. The bottle containing drug, i.e. ampule, is used for storing and transporting drug. When a user needs injection, it is necessary to cut and open the ampule at first, then to suck the drug from the ampule into injection tube through needle in preparation for injection. The operation for manipulating such kind of syringe is quite complicated, its working efficiency is low, particularly, during cutting and opening the ampule, the broken glass might be sucked into the injection tube and further injected into human body, so that a very serious consequence could result.

Accordingly, a kind of disposable syringe containing drug has been proposed, the injection tube of the syringe has a bypath linking up axially its front and back parts, both the inlet and the outlet of the by path are located on the inner surface of the injection tube, hence, the inner cavity of the injection tube is interpenetrated with the by path. The injection tube core consists of a rod, on which several pistons, for example 2 pistons, are provided at intervals, the axial interval between two pistons matches one between the inlet and the outlet of the bypath. When the injection tube core is movable and hermetically put in the injection tube, these pistons, for example two pistons, cover hermetically the inlet and the outlet respectively. The drug can be stored in the front part of the cavity of the injection tube, and the thinner is stored between two pistons. During application, when the injection tube core is being pulled out, its pistons don't seal the outlet and the inlet of the bypath any longer, at that time, in the front part of the injection tube vacuum results, because the needle is stopped by a rubber sealing stopper, and the thinner contained between the pistons inside the injection tube flows into the front part of the injection tube and mixes with the drug therein, then, remove the sealing stopper from the needle, push forward the injection tube core, after its front end has passed beyond the outlet of the bypath, the drug liquid can be forced for injection.

However, for the prior art disposable syringe integrating the syringe and the ampule into a whole, the structure is rather complicated, particularly, the stored drug is possible to be polluted, because the drug is isolated from outside only by the sealing between the pistons and the inner wall of the injection tube, hence the sealing is not very successful due to the movement of the pistons.

Therefore, it is an object of the present invention to provide a kind of disposable syringe integrating the syringe and the ampule into a whole, for which the structure is simple, and the stored drug can be sealed successfully and preserved not to be polluted and deteriorative for a long time.

SUMMARY OF THE INVENTION

With the above-mentioned aim, the present invention provides a syringe containing drug to be injected, the syringe includes an injection tube, a needle mounted at the front end of the injection tube, a rubber sealing jacket stopper jacketing on the peak of the needle and an injection tube core movably and hermetically put inside the injection tube, which is characterized in that said injection tube core consists of an ampule of cylindrical bottle shape and a piston, for said ampule, its back end is closed, and at its front end there are a flange and a neck portion, the central through hole of the flange and the neck portion is interpenetrated with the inner cavity of the bottle-shaped injection tube core; the outside top of said piston appears as a cone, and its outside lower part is a cylinder matching the inner wall of the injection tube, while the inside top of said piston appears as an inside cone, and the form of its inside lower part matches the shapes of the flange and the neck portion located at the front end of said ampule; at the cone-shaped top of said piston there is a slit linking up the inside and the outside of the top and inclined to the axis of the piston, so that a one-way valve which could be opened outwardly is formed at the cone-shaped top.

Said slit on the piston could be a partial arc, occupying an arc length of $\pi/4$ to $\pi/2$ radian.

Alternatively, the inside cone-shaped peak of the inside top of said piston is a concave sphere, a glass ball is located between said concave spherical peak and the outlet of the central through hole in the flange.

Alternatively, the inside cone-shaped peak of the inside top of said piston is a partial sphere which is convex inwardly.

On the cylindrical lower part of said piston there might be some ring grooves at intervals.

At the back end of said injection tube there are a protruding edge favorable for holding and pulling it with fingers, and an extending portion on which a cap is mounted to cover and seal the open end of the injection tube.

In the syringe containing drug to be injected according to the present invention, the liquid to be injected is contained in the injection tube core, when the injection tube core is pulled backwardly, at the front end of the inner cavity of the injection tube vacuum results, and the liquid in the injection tube core flows into the inner cavity of the injection tube through the one-way valve, which is formed by the inclined slit located on the top of the piston mounted at the front end of the injection tube core and could be opened outwardly. Remove the rubber sealing jacket stopper from the needle, push forward the injection tube core, then the liquid in the inner cavity of the injection tube sprays out under the press of the piston.

For such kind of syringe, not only the structure is simple, but also the drug sealed therein can be preserved successfully and the manipulation is convenient too.

BRIEF DESCRIPTION OF DRAWINGS

Further objects and advantages of the present invention will appear from the following description taken together with the accompanying diagrammatical drawings, where FIG. 1 is an assembly sectional view of the first embodiment of the syringe containing drug to be injected in accordance with the invention;

FIGS. 2 and 3 are respectively a front view and a top one of the piston in the syringe illustrated in FIG. 1;

FIG. 4 is a sectional view of the piston in the syringe illustrated in FIG. 1;

DETAILED DESCRIPTION OF THE PREFERRED EMBODIMENTS

Figure 5:
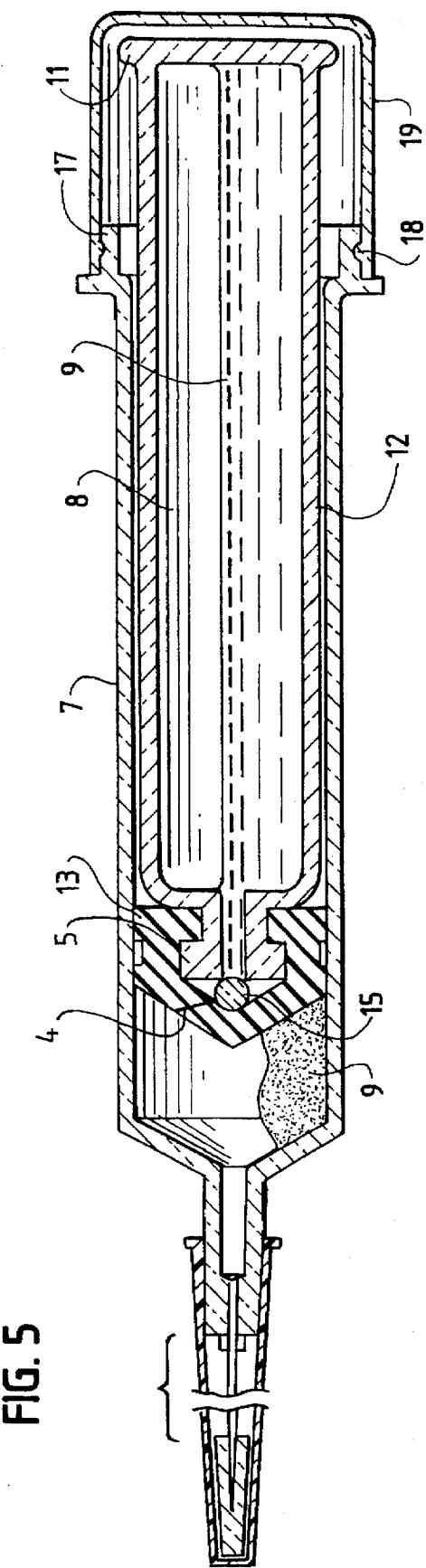
FIG. 5 is an assembly sectional view of the second embodiment of the syringe in accordance with the invention.

As shown in FIG. 1, in the first embodiment of the syringe in accordance with the invention, the syringe includes an injection tube 7, a needle 3 mounted at the front end of the injection tube 7, a rubber sealing jacket stopper 1 jacketing on the peak of the needle 3 and an injection tube core 8 movably and hermetically put inside the injection tube. On the needle 3 and the jacket stopper 1, a protecting case 2 is jacketed in order to protect the needle 3 against damage during transportation, the back end of the injection tube 7 is open, through which the injection tube core 8 can be inserted, and possesses a protruding edge 10 favorable for holding it with fingers. The injection tube core 8 includes an ampule 12 of cylindrical bottle shape and a piston 13, the back end of the ampule 12 is closed and possesses a flange plate 11 favorable for holding it with fingers, and at its front end there are a flange 5 and a neck portion 6, the central through hole inside the flange 5 and the neck portion 6 is interpenetrated with the inner cavity of the injection tube core 8. The piston 13 is jacketed on said flange 5 and neck portion 6, the outside top of the piston 13 appears as a cone, and its outside lower part is a cylinder matching the inner wall of the injection tube 7, on the lower part of the cylinder there might be one or more ring grooves 14 at axial intervals to form labyrinth sealing, so that the sealing will have better effect during sliding of the piston 13(refer to FIGS. 2, 3 and 4). The inside top of the piston 13 appears as an inner cone and the form of its inside lower part matches the shapes of the flange 5 and the neck portion 6 located at the front end of the ampule 12. At the cone-shaped top of the piston 13 there is a slit 4 inclined to the axis of the piston 13, the slit 4 is a partial arc occupying an arc length of $\pi/4$ to $\pi/2$ radian in the circumferential direction, so that a one-way valve which could be opened outwardly is formed at the cone-shaped top of the piston 13. The drug liquid to be injected is preserved inside the ampule 12.

During application, at first pull the ampule 12 backwardly, because the needle 3 is stopped by the jacket stopper 1, at the front end of the injection tube 7, i.e. in front of the piston 13, vacuum results when the piston 13 slides on the inner wall of the injection tube 7, and the drug liquid 9 contained inside the ampule 12 flows into the inner cavity of the injection tube 7 through the one-way valve formed by the slit 4 on the piston 13. Then remove the protecting case 2 and jacket stopper 1, push forward the ampule 12, the drug liquid sprays out from the needle 3 under the press of the piston 13.

Figure 6:
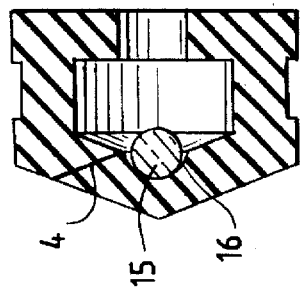
FIG. 6 is a sectional view of the piston in the syringe illustrated in FIG. 5, where the sealed glass ball is shown.

FIG. 5 shows the syringe of the second embodiment in accordance with the invention. This embodiment is basically the same as the first one, the only difference lies in that there is a spherical concavity at the inside top of the piston 13, i.e. the inside top is a concave sphere (refer to FIG. 6), and a glass ball 15 is located between the concavity 16 and the flange 5 at the front end of the injection tube core 8. The glass ball 15 can prevent drug from deterioration due to its long term contacting with the rubber piston. On the protruding edge 10 of the injection tube 7 there is a axially extending portion 17, on which a push-button structure 18 is provided, and a cap 19 is mounted on the extending portion 17 using its push-button structure. The drug liquid 9 is contained in the ampule 12, and the drug powder 9' in the inner cavity at the front end of the injection tube 7.

Figure 7:
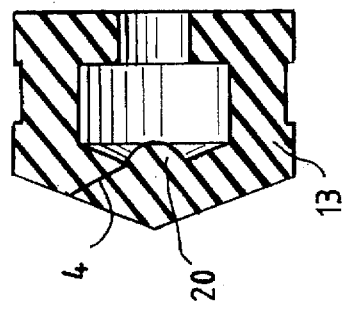
FIG. 7 is a sectional view of the piston of the third embodiment in accordance with the invention.

FIG. 7 is a sectional view of the piston 13 of the third embodiment in accordance with the invention. This embodiment is basically the same as the first one, the only difference lies in that at the inside top of the piston 13 there is a partially spherical portion 20, which is convex inwardly. When the piston 13 is mounted on the flange 5 and the neck portion 6 at the front end of the ampule 12 of the injection tube core 8, the partially spherical portion 20 covers hermetically the through hole in the flange 5, so that seals the ampule 12. When the ampule 12 is pulled backwardly, the partially spherical portion 20 doesn't cover the through hole in the flange 5 any longer because the one-way valve formed by the slit 4 turns to open outwardly, drug liquid flows from the inside of the ampule 12 into the injection tube 7 and is ready for injection.

What is claimed is:

1. An improved syringe containing drug to be injected, the improvement comprising an injection tube having a front end and an open back end, a needle mounted at the front end of the injection tube, a rubber sealing jacket stopper jacketing the peak of the needle and an injection tube core movably and hermetically put inside the injection tube, said injection tube core consisting of an ampule of cylindrical bottle shape, an inner cavity, and a piston, the back end of said ampule is closed, toward the front end of said ampule there is a neck portion, and immediately forward of said neck portion, the front end of said ampule terminates at a flange, said neck portion and said flange having a central through hole therein;

the central through hole of said flange and said neck portion is coextensive with the inner cavity of said bottle-shaped injection tube core;

said piston has a forward outside end which appears as a cone, a rear outside part which is a cylinder matching the inner wall of said injection tube, a forward inside end which appears as an inner cone, and a rear inside part having a form which matches the shapes of said flange and said neck portion located at the front end of said ampule;

at said cone-shaped forward end of said piston there is a slit linking up the forward outside end and the forward inside end and inclined to a longitudinal axis of said piston, so that a one-way valve which could be opened outwardly is formed at said cone-shaped forward end, said slit on said piston being a partial arc, occupying an arc length of $\pi/4$ to $\pi/2$ radian.

2. A syringe as claimed in claim 1, wherein said inside cone-shaped peak of said forward inside end of said piston includes a concave hemi-spherical portion therein, a glass ball is located between the apex of said concave hemi-spherical portion and the outlet of said central through hole in said flange.

3. A syringe as claimed in claim 1, wherein said inside cone-shaped peak of said forward inside end of said piston includes a rearwardly projecting convex hemi-spherical portion thereon.

* * * * *

UNITED STATES PATENT AND TRADEMARK OFFICE
CERTIFICATE OF CORRECTION

PATENT NO. : 5,695,465
DATED : December 9, 1997
INVENTOR(S) : Jinyou Zhu

It is certified that error appears in the above-indentified patent and that said Letters Patent is hereby corrected as shown below:

On the title page: Item [76], "1-301, Kunminglu Road" should be --78-1-301, Kunminglu Road--.

Signed and Sealed this

Twenty-sixth Day of May, 1998

Attest:

BRUCE LEHMAN

Attesting Officer          Commissioner of Patents and Trademarks